US00PP31834P2

(12) United States Plant Patent
Zary

(10) Patent No.: US PP31,834 P2
(45) Date of Patent: Jun. 2, 2020

(54) CRAPE MYRTLE PLANT NAMED 'GARZARNOBEMAGEN'

(50) Latin Name: *Lagerstroemia indica*
Varietal Denomination: GARzarnobemagen

(71) Applicant: Early Morning LLC, Greendale, IN (US)

(72) Inventor: Keith W. Zary, Missoula, MT (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/602,340

(22) Filed: Sep. 17, 2019

(51) Int. Cl.
*A01H 5/00* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/00
See application file for complete search history.

*Primary Examiner* — Kent L Bell
(74) *Attorney, Agent, or Firm* — Barbara Campbell; Cochran Freund & Young LLC

(57) ABSTRACT

A new and distinct variety of crape myrtle plant, an upright, and compact shrub having numerous flowers on panicles and resistance to leaf spot and powdery mildew strains found in Ohio and California, is disclosed.

2 Drawing Sheets

Genus and species: *Lagerstroemia indica.*
Denomination: 'GARzarnobemagen'.

BACKGROUND

'GARzarnobemagen' is a new and distinct variety of crape myrtle. 'GARzarnobemagen' originated from a controlled cross in August 2011 in Tipp City, Ohio between the female parent, an unnamed and unpatented seedling derived from the cross between the crape myrtle plants 'Centennial' (unpatented) and 'Dynamite' (U.S. Plant Pat. No. 10,269) and the male parent, 'Tightwad Red' (U.S. Plant Pat. No. 14,975).

The resulting seeds from the cross were collected in August 2011 and planted and evaluated in Tipp City, Ohio. 'GARzarnobemagen' was selected in July 2012 from the population of seedlings in Tipp City, Ohio. 'GARzarnobemagen' was first asexually propagated in July 2014 in Tipp City, Ohio from softwood cuttings.

Other subsequent asexual propagations were conducted in controlled environments in Tipp City, Ohio and demonstrate that 'GARzarnobemagen' reproduces true to type in successive generations of asexual reproduction via softwood cuttings.

SUMMARY

The following are the most outstanding and distinguishing characteristics of this new variety when grown under normal horticultural practices in Tipp City, Ohio.

1. An upright, and compact shrub having numerous flowers on panicles; and
2. Resistance to leaf spot and powdery mildew strains found in Ohio and California.

DESCRIPTION OF THE PHOTOGRAPHS

This new crape myrtle plant is illustrated by the accompanying photographs which show the plant's overall plant habit including form, foliage, and flowers. The photographs are of a 4-year old plant grown outdoors in Tipp City, Ohio in August 2019. The colors shown are as true as can be reasonably obtained by conventional photographic procedures.

DETAILED DESCRIPTION

Figure 1:
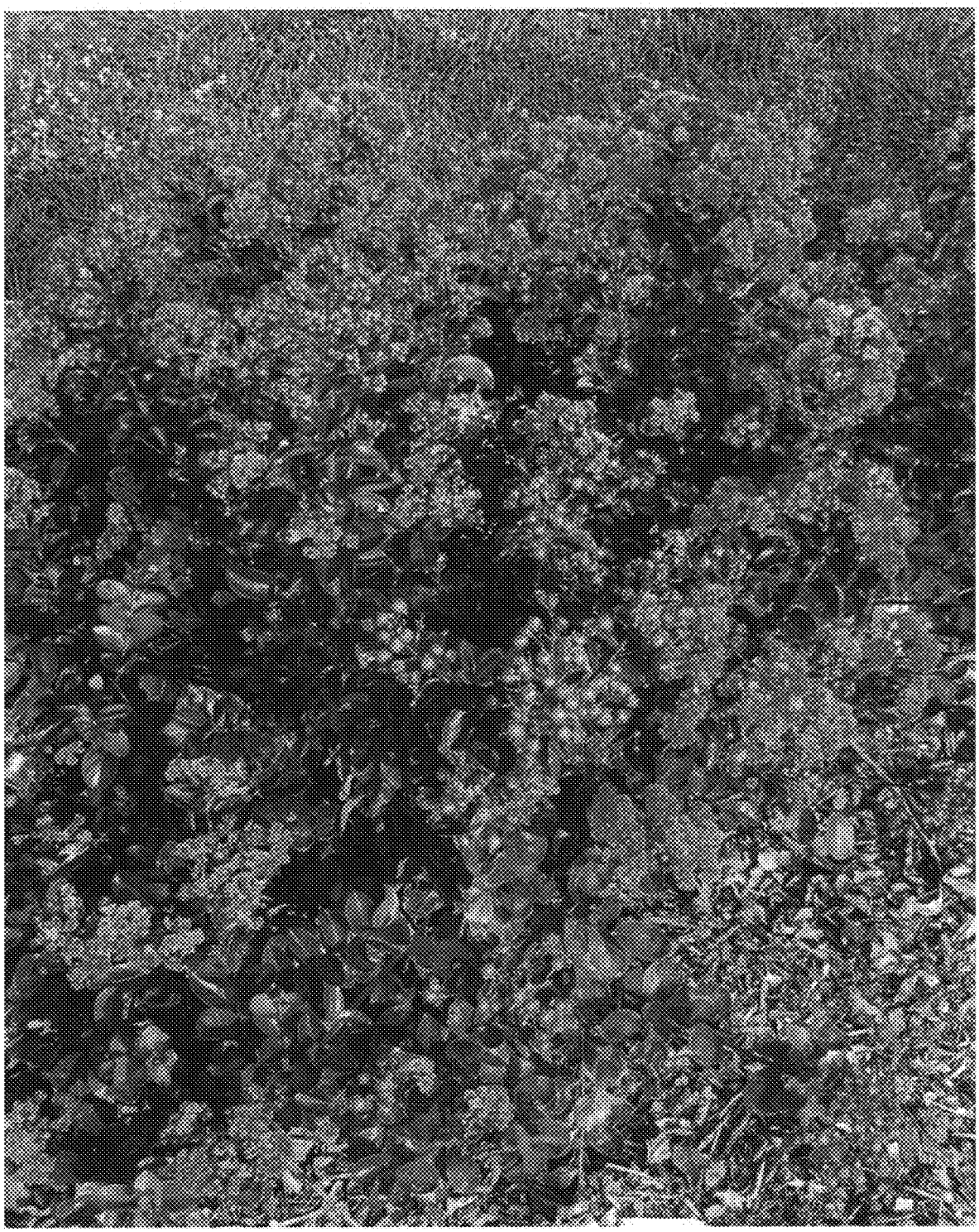
FIG. 1 shows the overall plant habit of 'GARzarnobemagen'.
Figure 2:
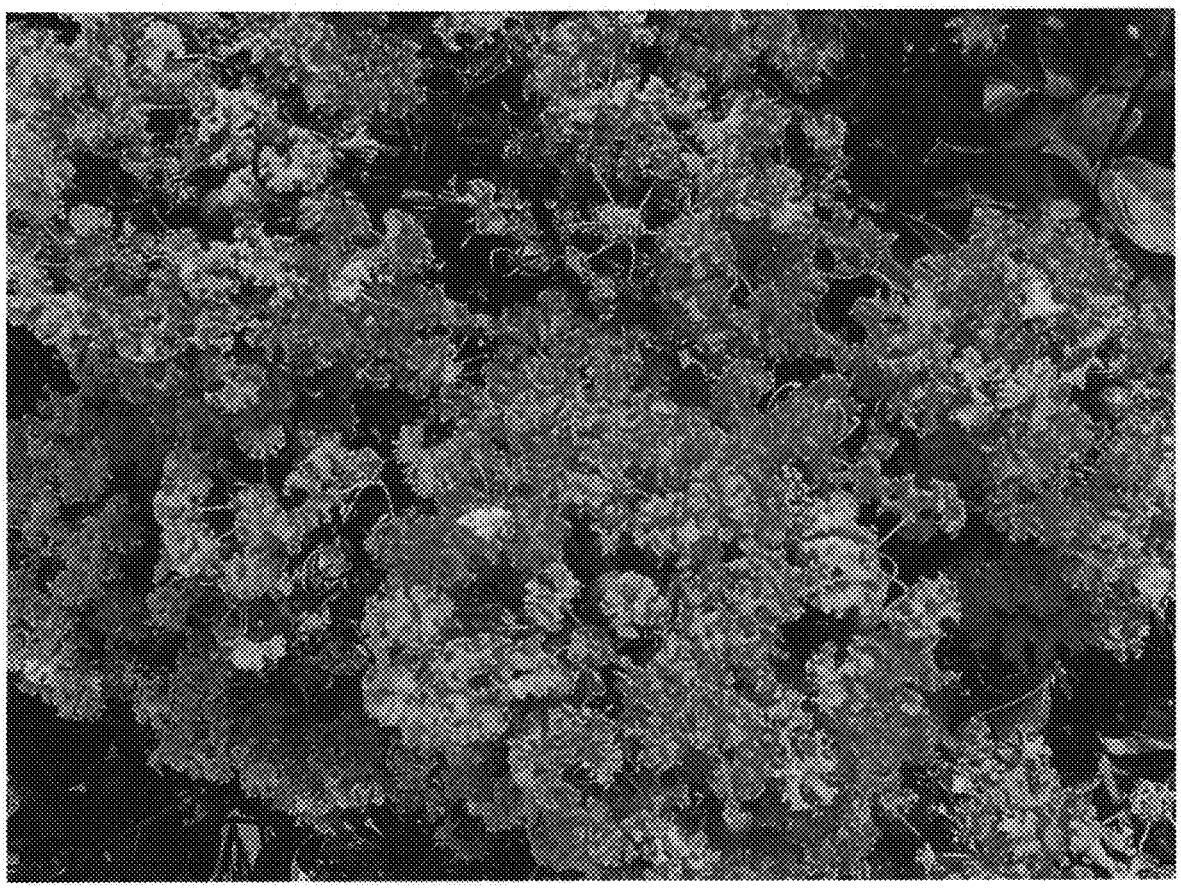
FIG. 2 shows a close-up of the individual flowers, buds, foliage, and bark of the plant.

The following detailed descriptions set for the distinctive characteristics of 'GARzarnobemagen'. The data which define these characteristics were collected outdoors in Tipp City, Ohio. Plants were propagated in a greenhouse in 2014 and transplanted to an outdoor field in Tipp City, Ohio in May 2015 and evaluated each year thereafter. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:
- *Family.*—Lythraceae.
- *Species.*—*Lagerstroemia indica.*
- *Variety.*—'GARzarnobemagen'.

Parentage:
- *Female parent.*—An unnamed and unpatented seedling derived from the cross between the crape myrtle plants 'Centennial' and 'Dynamite' (U.S. Plant Pat. No. 10,269).
- *Male parent.*—'Tightwad Red' (U.S. Plant Pat. No. 14,975).

Propagation:
- *Type.*—Softwood cuttings.
- *Time to initiate roots.*—Three weeks.
- *Time to produce a rooted young plant.*—8 to 10 weeks.
- *Root description.*—Fine and fibrous.
- *Rooting habit.*—Well-branched.

Plant description:
- *Plant form and growth habit.*—Upright and compact.
- *Branching habit.*—Free-branching, growing upward and outward.

*Plant height.*—90.0 cm.
*Plant diameter* (*area of spread*).—75.0 cm.

Lateral branch description:
*Length.*—75.0 cm.
*Diameter.*—10.0 mm at the base and 6.0 mm at the top.
*Internode length.*—2.4 cm.
*Strength.*—Strong.
*Texture, immature.*—Pubescent.
*Texture, mature.*—Woody.
*Color, immature.*—RHS 181A and fading rapidly to RHS 179C with longitudinal carinae RHS 179B.
*Color, mature.*—Between RHS N199C and RHS N199D.

Bark:
*Immature stem color.*—RHS 181A fading rapidly to RHS 179C with RHS 179B ridges.
*Mature stem color.*—RHS N199C to RHS 199D.

Leaf:
*Arrangement.*—Sub-opposite to alternate.
*Length.*—5.3 cm.
*Width.*—4.0 cm.
*Shape.*—Elliptic.
*Apex.*—Acute to rounded.
*Base.*—Cuneate.
*Margin.*—Entire, ciliolate.
*Texture* (*both upper and lower surfaces*).—Lustrous, leathery.
*Venation pattern.*—Pinnate, puberulent.
*Venation color.*—Upper surface: RHS 147B. Lower surface: RHS 147C with blush of RHS 178D.
*Immature leaf color.*—Upper surface: RHS 139A overlaid with RHS 177A and very quickly changing to RHS 139A. Lower surface: RHS 177A and changes more slowly to RHS 147B.
*Mature leaf color.*—Upper surface: RHS 139A. Lower surface: RHS 147B.
*Petioles.*—Length: 1.0 mm. Width: 2.0 mm. Color: RHS 178D. Texture: Puberulent.

Flower:
*Flower arrangement and flowering habit.*—Panicle averaging about 80 to 90 flowers on terminals.
*Natural flowering season.*—Late July through August in Southwest Ohio.
*Fragrance.*—Little to none.
*Inflorescence height.*—18.0 cm.
*Inflorescence diameter.*—14.0 cm.
*Flower diameter.*—4.0 cm.
*Flower length.*—2.0 cm.
*Flower buds.*—Globose; smooth/glabrous; 7.0 mm length and 8.0 mm wide.
*Flower bud color.*—RHS 184C.

Petals:
*Quantity.*—6 per flower.
*Lobe length.*—1.4 cm.
*Lobe width.*—1.2 cm.
*Lobe shape.*—Cordate to sagittate.
*Apex.*—Rounded.
*Base.*—Adnate to sepal.
*Margin.*—Ruffled.
*Color* (*both upper and lower surfaces*).—RHS N77A to RHS N77B.

Sepals:
*Quantity and arrangement.*—6 and fused at the base.
*Length.*—Above the fused portion, the length is 3.0 mm.
*Width.*—Above the fused portion, the width is 3.0 mm.
*Shape.*—Triangular.
*Apex.*—Acute.
*Base.*—Fused.
*Margin.*—Entire.
*Color.*—Upper surface: RHS 184C. Lower surface: RHS 145C.

Peduncles:
*Length.*—18.0 cm.
*Diameter.*—4.0 mm at the base, and 2.5 mm at the terminal portion.
*Strength.*—Strong.
*Texture.*—Rough, terete, four longitudinal carinae.
*Color.*—RHS 184D.

Pedicels:
*Length.*—4.0 mm.
*Diameter.*—1.0 mm.
*Strength.*—Strong.
*Texture.*—Terete.
*Color.*—RHS 184D.

Reproductive organs:
*Androecium.*—Quantity of stamens per flower: About 26; 6 long anthers and about 20 shorter anthers. Filament length: 14.0 mm for the longer ones and 7.0 mm for the shorter ones. Anther shape: Oblong. Anther length: 1.4 mm. Anther color: RHS 13C. Amount of pollen: Abundant. Pollen color: RHS 15C.
*Gynoecium.*—Quantity of pistils per flower: 1. Pistil Length: 13.0 mm. Style length: 12.0 mm. Style color: RHS 184B and changing to RHS 184A towards the base. Stigma color: RHS 184A. Stigma shape: Globose. Ovary color: RHS 145D.

Fruit and seed set: Seed is present; it is globose in shape, a 6-valved dehiscent capsule that is about 8.0 mm wide and 7.0 mm in length; color is RHS 200C to RHS 200D.

Disease and insect resistance: Resistant to powdery mildew strains *Erysiph* found in Ohio and California and resistant to leaf spot, *Cercospora.*

COMPARISON WITH PARENTAL AND COMMERCIAL LINES

Table 1 shows a comparison of differences between 'GARzarnobemagen' and both parental lines.

TABLE 1

Comparison with Parental Lines

| Characteristic | 'GARzarnobemagen' | Female parent, un-named crape myrtle seedling | Male parent, 'Tightwad Red' |
|---|---|---|---|
| Flower color | RHS N77A to RHS N77B | RHS 49C | RHS 47B |
| Plant habit and size | Upright and 90 cm by 75 cm | Upright and 150 cm by 125 cm | Spreading and 90 cm by 120 cm |

Table 2 shows a comparison of the differences between 'GARzarnobemagen' and the commercial crape myrtle variety 'Spiced Plum' (U.S. Plant Pat. No. 29,478).

TABLE 2

Comparison with Commercial Line

| Characteristic | 'GARzarnobemagen' | 'Spiced Plum' |
|---|---|---|
| Flower color | RHS N77A to RHS N77B | RHS 72A to RHS 72B |
| Plant habit and size | Upright and 90 cm by 75 cm | Spreading and 52 cm by 58 cm |

I claim:

1. A new and distinct variety of crape myrtle plant designated 'GARzarnobemagen' as illustrated and described herein.

* * * * *